US012208104B2

(12) United States Patent
Tseng et al.

(10) Patent No.: US 12,208,104 B2
(45) Date of Patent: Jan. 28, 2025

(54) PHARMACEUTICAL COMPOSITIONS SUITABLE FOR ARTICULAR DELIVERY AND USE THEREOF IN TREATMENT OF JOINT PAIN

(71) Applicants: TAIWAN LIPOSOME CO., LTD., Taipei (TW); TLC BIOPHARMACEUTICALS, INC., South San Francisco, CA (US)

(72) Inventors: Yun-Long Tseng, Taipei (TW); Sheue-Fang Shih, Taipei (TW); Po-Chun Chang, Taipei (TW); Lo Chang, Taipei (TW)

(73) Assignees: Taiwan Liposome Co., Ltd., Taipei (TW); TLC Biopharmaceuticals, Inc., South San Francisco, CA (US)

( * ) Notice: Subject to any disclaimer, the term of this patent is extended or adjusted under 35 U.S.C. 154(b) by 1004 days.

(21) Appl. No.: 17/272,387

(22) PCT Filed: Sep. 16, 2019

(86) PCT No.: PCT/US2019/051247
§ 371 (c)(1),
(2) Date: Mar. 1, 2021

(87) PCT Pub. No.: WO2020/056399
PCT Pub. Date: Mar. 19, 2020

(65) Prior Publication Data
US 2021/0338688 A1   Nov. 4, 2021

Related U.S. Application Data

(60) Provisional application No. 62/731,941, filed on Sep. 16, 2018.

(51) Int. Cl.
| | |
|---|---|
| *A61K 31/573* | (2006.01) |
| *A61K 9/00* | (2006.01) |
| *A61K 31/58* | (2006.01) |
| *A61K 47/24* | (2006.01) |
| *A61K 47/28* | (2006.01) |
| *A61P 19/02* | (2006.01) |

(52) U.S. Cl.
CPC .......... *A61K 31/573* (2013.01); *A61K 9/0019* (2013.01); *A61K 31/58* (2013.01); *A61K 47/24* (2013.01); *A61K 47/28* (2013.01); *A61P 19/02* (2018.01)

(58) Field of Classification Search
CPC .... A61K 31/573; A61K 19/02; A61K 9/0019; A61K 31/58; A61K 47/24; A61K 47/28
See application file for complete search history.

(56) References Cited

U.S. PATENT DOCUMENTS

| | | | |
|---|---|---|---|
| 2005/0152962 A1 | 7/2005 | Metselaar | |
| 2015/0011520 A1 | 1/2015 | Hong et al. | |
| 2017/0367979 A1* | 12/2017 | Hong .................. | A61K 31/573 |

FOREIGN PATENT DOCUMENTS

| | | |
|---|---|---|
| CN | 105377238 A | 3/2016 |
| TW | 201338806 A | 10/2013 |
| TW | 201406404 A | 2/2014 |
| WO | 2014/008469 A2 | 1/2014 |

OTHER PUBLICATIONS

Feng et al., Optimization on Preparation Conditions of Salidroside Liposome and Its Immunological Activity on PCV-2 in Mice, Evidence-based Complementary and Alternative Medicine, vol. 2015, Article ID 178128, 1-12.
International Search Report and Written Opinion of PCT/US2019/051427, mailed on Dec. 11, 2019.
Altman et al: "Development of Criteria for the Classification and Reporting of Osteoarthritis": Arthritis Rheum. 1986; vol. 29, No. 8:1039-1049 [11 pages].
Barenholtz et al.: "A New Method for Preparation of Phospholipid Vesicles (Liposomes)—French Press": FEBS Letters (Mar. 1979) vol. 99, No. 1: 210-214 [5 pages].
Brunner et al.: "Single Bilayer Vesicles Prepared Without Sonication Physico-Chemical Properties": Biochim. Biophys. Acta, (1976) 455: 322-331 [10 pages].
Clinical trial NCT02803307: "Single-Dose Administration Trial of TLC599 in Osteoarthritis of the Knee": May 6, 2022 [8 pages].
Coopman et al., "Identification of cross-reaction patterns in allergic contact dermatitis from topical corticosteroids" British Journal of Dermatology (1989); 121(1):27-34 [9 pages].
Dreamer: "Preparation and Properties of Ether-Injection Liposomes": Acad. Sci. (1978) 308: 250-258 [9 pages].
Hope et al.: "Production of large unilamellar vesicles by a rapid extrusion procedure. Characterization of size distribution, trapped vol. and ability to maintain a membrane potential", Biochim. Biophys. Acta 812 (1985):55-65 [11 pages].
Huang: "Studies on Phosphatidylcholine Vesicles. Formation and Physical Characteristics": Biochemistry (1969) 8: 344-352 [9 pages].
Kellgren et al.: "Rheumatism in Miners Part II: X-Ray Study": Brit. J. industr. Med. 1952; 9:197-207 [11 pages].
Kremer et al.: "Vesicles of Variable Diameter Prepared by a Modified Injection Method": Biochemistry (1977) vol. 16, No. 17: pp. 3932-3935. [4 pages].
Pick: "Liposomes with a Large Trapping Capacity Prepared by Freezing and Thawing of Sonioated Phospholipid Mixtures": Archives of Biochemistry and Biophys. vol. 212, No. 1, Nov. 1981: pp. 186-194. [9 pages].

(Continued)

*Primary Examiner* — Shirley V Gembeh
(74) *Attorney, Agent, or Firm* — Leason Ellis LLP

(57) ABSTRACT

The present disclosure relates to pharmaceutical composition for the treatment of joint pain. The composition contains a lipid mixture comprising one or more phospholipids; and an effective amount of a therapeutic agent or a pharmaceutically acceptable salt thereof, where the total amount of phospholipids in said composition is about 20 mM to about 150 mM, optionally 70 mM to 110 mM. Also provided is the use of the pharmaceutical composition in the treatment of joint pain by articular injection.

13 Claims, 11 Drawing Sheets

(56) References Cited

OTHER PUBLICATIONS

Szoka et al.: "Comparative Properties and Methods of Preparation of Lipid Vesicles (Liposomes)": Ann. Rev. Biophys. Bioeng. (1980) 9:467-508 [42 pages].
Szoka et al.: "Preparation of Unilamellar Liposomes of Intermediate Size (0.1-0.2 μm) By a Combination of Reverse Phase Evaporation and Extrusion Through Polycarbonate Membranes": Biochim. Biophys. Acta. (1980) 601: 559-571 [13 pages].
Wernecke et al.: "The Effect of Intra-articular Corticosteroids on Articular Cartilage": The Orthopaedic Journal of Sports Medicine, 3(5), (2015) (DOI: 10.1177/2325967115581163) [7 pages].

* cited by examiner

PHARMACEUTICAL COMPOSITIONS SUITABLE FOR ARTICULAR DELIVERY AND USE THEREOF IN TREATMENT OF JOINT PAIN

BACKGROUND

Technology Field

The present disclosure relates to pharmaceutical compositions suitable for articular delivery and methods to treat joint pain with a balance between enhanced therapeutic efficacy and minimized side effects of a therapeutic agent.

Description of Related Art

Therapy for controlling joint pain has been developed to reduce joint inflammation and pain by the local delivery of a therapeutic agent, particularly to an anti-inflammatory agent, to the joint tissue. It has been shown to be effective at temporarily alleviating joint pain associated with osteoarthritis and other inflammatory disorders.

Although the general methods of delivery of therapeutic agents to joint tissue are well documented in the literature, these generally have limited efficacy. Various factors can affect pharmacokinetics and pharmacodynamics of the therapeutic agent in the joint, including but not limited to, chemical physical properties of selected therapeutic agents, clearance action of particulate vehicle by macrophage and characteristics of the delivery platform.

In view of the deficiencies outlined above, there is a need for an improved therapy for treating joint pain with a sustained therapeutic efficacy (3-6 months), enhanced therapeutic efficacy, preferably in conjunction with reduced side effect profile, especially a reduction of cartilage damage, chondrocyte damage, and/or abnormal plasma cortisol value. The present disclosure addresses this need and other needs.

SUMMARY

According to one embodiment of the present disclosure, provided is a pharmaceutical composition suitable for articular delivery of a therapeutic agent comprising:
(a) a lipid mixture comprising one or more phospholipids; and
(b) an effective amount of the therapeutic agent or a pharmaceutically acceptable salt thereof;
wherein the total amount of the one or more phospholipids in said pharmaceutical composition is about 20 μmol to about 150 μmol per 1 mL (milliliter) of the pharmaceutical composition.

Also provided are methods of treating joint pain comprising: intra-articularly administering to a subject in need of such treatment an effective amount of a pharmaceutical composition in accordance with the present disclosure.

Also provided is use of a pharmaceutical composition for manufacture of an articular injection for treatment of joint pain, wherein the pharmaceutical composition comprising:
(a) a lipid mixture comprising one or more phospholipids; and
(b) an effective amount of the therapeutic agent or a pharmaceutically acceptable salt thereof; wherein the total amount of the one or more phospholipids per each articular injection is about 20 μmol to equal to or less than about 150 μmol and wherein the efficacy of said pharmaceutical composition is enhanced, relative to the efficacy of a pharmaceutical composition having more than about 150 μmol of phospholipid per each articular injection.

This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

DETAILED DESCRIPTION OF THE EMBODIMENTS

Definition

Figure 1:
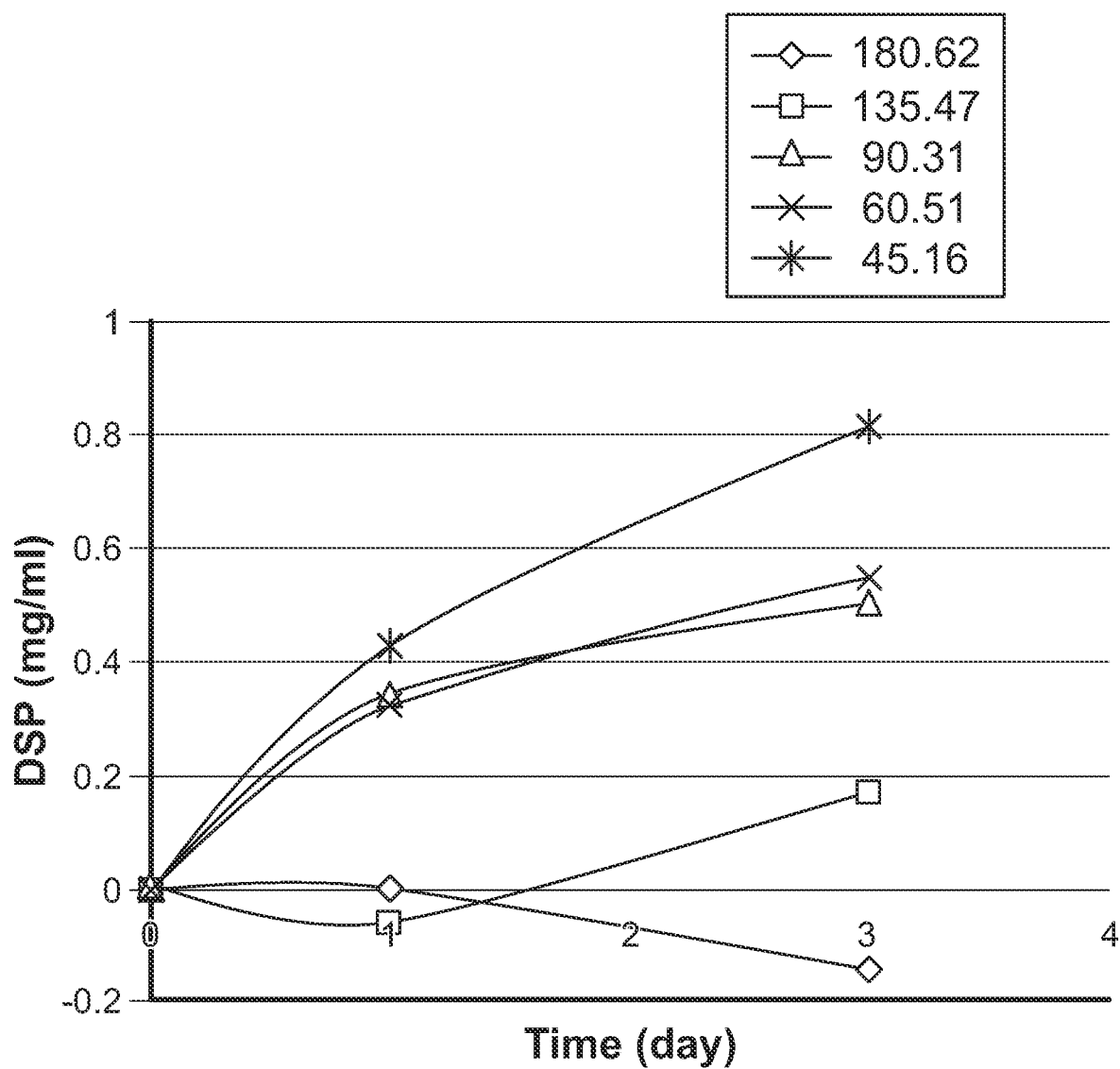
FIG. 1 is a line graph showing the release profiles of the pharmaceutical compositions according to the present application with different amounts of phospholipid.

As employed above and throughout the disclosure, the following terms, unless otherwise indicated, shall be understood to have the following meanings.

As used herein, the singular forms "a," "an," and "the" include the plural reference unless the context clearly indicates otherwise.

All numbers herein may be understood as modified by "about." As used herein, the term "about" refers to a range of ±10% of a specified value.

The term "articular injection" as used herein, encompasses local injection at or near the site of joint pain, intra-articular injection or periarticular injection.

An "effective amount," as used herein, refers to a dose of the pharmaceutical composition that is sufficient to reduce the symptoms and signs of disease causing the joint pain, such as pain, stiffness and swelling of the joint, and to reduce the side effect associated with injection of the therapeutic agent. The reduction can be about 10%, 20%, 30%, 40%, 50%, 60%, 70%, 80%, 90%, 100%, or any amount of reduction in between.

The term "treating," "treated," or "treatment" as used herein includes preventative (e.g. prophylactic), slowing, arresting or reversing progressive structural tissue damage causing joint pain. Throughout this application, by treating is meant a method of reducing, alleviating, inhibiting or delaying joint pain or the complete amelioration of joint pain as detected by art-known techniques. These include, but are not limited to, clinical examination, imaging or analysis of serum or joint aspirate (for example, rheumatoid factors, erythrocyte sedimentation rate), to name a few. For example, a disclosed method is considered to be a treatment if there is about 1%, 5%, 10%, 20%, 30%, 40%, 50%, 60%, 70%, 80%, 90% or 100% reduction of joint pain in a subject when compared to the subject prior to treatment or control subjects. The treatment includes single articular injection or multiple articular injections within a desired interval.

The term "subject" can refer to a vertebrate having joint pain or to a vertebrate deemed to be in need of treatment for joint pain. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "joint pain" refers to a joint disorder or condition that involves inflammation and/or pain of one or more joints. The term "joint pain," as used herein, encompasses a variety of types and subtypes of arthritis of various etiologies and causes, either known or unknown, including, but not limited to, rheumatoid arthritis, osteoarthritis, infectious arthritis, psoriatic arthritis, gouty arthritis, and lupus-related arthritis or painful local tissues affected by bursitis, tenosynovitis, epicondylitis, synovitis and/or other disorders.

"Pharmaceutically acceptable salts" of the therapeutic agent of the present disclosure are salts of an acidic therapeutic agent formed with bases, namely base addition salts such as alkali and alkaline earth metal salts, such as sodium, lithium, potassium, calcium, magnesium, as well as 4 ammonium salts, such as ammonium, trimethyl-ammonium, diethylammonium, and tris-(hydroxymethyl)-methyl-ammonium salts. Similarly acid addition salts, such as of mineral acids, organic carboxylic and organic sulfonic acids, e.g., hydrochloric acid, methanesulfonic acid, maleic acid, are also possible provided to a basic therapeutic agent.

Pharmaceutical Composition

In one aspect, the present disclosure provides a pharmaceutical composition comprising a lipid mixture comprising one or more phospholipids and an effective amount of a therapeutic agent or a pharmaceutically acceptable salt thereof, wherein the total amount of phospholipids in each ml of the pharmaceutical composition is about 20 µmol to 150 µmol per 1 mL.

In one embodiment, the pharmaceutical compositions described herein sustained the release of the therapeutic agent for up to 3 months, 4 months, 5 months or 6 months, two weeks, three weeks, four weeks, five weeks, six weeks, seven weeks, eight weeks, night weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks and twenty-three weeks.

In another embodiment, the efficacy of the pharmaceutical composition disclosed herein is increased, relative to the efficacy of a pharmaceutical composition having more than 150 µmol of phospholipids per 1 mL of pharmaceutical composition. In yet another embodiment, the pharmaceutical composition disclosed herein sustains the therapeutic efficacy of the therapeutic agent and reduces the side effects associated with the therapeutic agent.

In one embodiment, the total amount of phospholipids is about 50 µmol to less than about 140 µmol per 1 mL of pharmaceutical composition. In another embodiment, the total amount of phospholipids is about 45 µmol to less than about 135 µmol per 1 mL of pharmaceutical composition. In another embodiment, the total amount of phospholipids is about 50 µmol to less than about 120 µmol per 1 mL of pharmaceutical composition. In another embodiment, the total amount of phospholipids is about 60 µmol to less than about 110 µmol per 1 mL of pharmaceutical composition.

In one embodiment, the pharmaceutical composition further comprising at least one pharmaceutically acceptable excipient, diluent, vehicle, carrier, medium for the active ingredient, a preservative, cryoprotectant or a combination thereof.

In one embodiment, the pharmaceutical composition of the present disclosure is prepared by mixing one or more phospholipids, with or without cholesterol, and one or more buffers to form liposomes, lyophilizing the liposomes with one or more bulking agents to form a lipid mixture in a form of cake and reconstituting the lipid mixture cake with a solution containing the therapeutic agent to form an aqueous suspension.

In another embodiment, the pharmaceutical composition of the present disclosure is prepared by mixing one or more phospholipids, with or without cholesterol, in a solvent then removing the solvent to form a lipid mixture in a form of powder or film and reconstituting the lipid mixture powder or film with a solution containing the therapeutic agent to form an aqueous suspension. In another embodiment, the pharmaceutical composition of the present disclosure is prepared by mixing one or more phospholipids, with or without cholesterol, in a solvent then followed by the injection of the dissolved lipid solution into an aqueous solution to form liposomes. Liposomes are then sized down by filtering through track-etched polycarbonate membranes. Solvent is removed by diafiltration against buffer by means of a semi-automated tangential-flow filtration (TFF) system. The dialfiltrated liposome solution was then lyophilized in a form of powder and reconstituting the lipid mixture powder or film with a solution containing the therapeutic agent to form an aqueous suspension.

In some embodiments, the pharmaceutical composition of the present disclosure comprises about 10% to about 50% of lipid-associated therapeutic agent or about 50% to about 90% of non-associated therapeutic agent. The term "non-associated form" refers to the therapeutic agent molecules separable via gel filtration from the phospholipid/cholesterol fraction of the pharmaceutical composition and provides immediate release component. In other embodiments, the weight ratio of the combination of the phospholipid and cholesterol to the therapeutic agent is about 5-80 to 1. In yet another embodiment, the weight ratio of the combination of the phospholipid and cholesterol to the therapeutic agent is about 5-40 to 1. For example, the weight ratio of the combination of the phospholipid and cholesterol to the therapeutic agent can be about 5, 10, 15, 20, 25, 30, 35, 40, 45, 50, 55, 60, 65, 70, 75 or 80 to 1.

In some embodiments, the therapeutic agent of the pharmaceutical composition of the present disclosure is at a concentration of at least or about 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM or 35 mM; and optionally ranging from about 10 mM to about 40 mM, from about 15 mM to about 40 mM, 20 mM to about 40 mM, from about 15 mM to about 35 mM, from about 15 mM to about 30 mM, 15 mM to about 25 mM, or from about 20 mM to about 25 mM.

In some embodiments, the total amount of the pharmaceutical composition for each administration ranges from about 0.5 mL to about 1.5 mL, and optionally about 1.0 mL.

Lipid Mixture

The lipid mixture of the pharmaceutical composition provided herein refers to a phospholipid or a mixture of phospholipids. The lipid mixture may be, but not limited to, in a form of film, cake, granules or powders before being added to the pharmaceutical composition.

In one embodiment, the phospholipid or the mixture of phospholipids, with or without cholesterol, are pre-formed into liposomes before further processing into a lipid mixture.

In another embodiment, the phospholipid or mixture of phospholipids, with or without cholesterol, are not pre-formed into liposomes before further processing into a lipid mixture.

The liposomes are nano-sized and comprise a lipid unilayer or a lipid bilayer surrounding an internal aqueous agent-carrying component. Non-limiting examples of liposomes include small unilamellar vesicles (SUV), large unilamellar vesicles (LUV), multivesicular liposome (MVL) and multi-lamellar vesicles (MLU).

The lipid mixture can be prepared from a variety of lipids capable of either forming or being incorporated into a unilayer or bilayer structure. The lipids used in the present disclosure include one or more phospholipids, including but are not limited to, phosphatidylcholine (PC), phosphatidylglycerol (PG), phosphatidylethanolamine (PE), phosphatidylserine (PS), phosphatidic acid (PA), phosphatidylinositol (PI) or combinations thereof. In some embodiments, the lipid mixture comprises egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI) or combinations thereof. In another embodiments, the lipid mixture comprises dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), polyethyleneglycol distearoylphosphatidylethanolamine (PEG-DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), or combinations thereof.

In some embodiments, the lipid mixture comprises a first phospholipid and a second phospholipid. In some embodiments, the first phospholipid is selected from the group consisting of EPC, EPE, SPC, SPE, DPPC, DOPC, DMPC, HEPC, HSPC, DSPC, DOPE, PSPC, MOPE, POPC; and the second phospholipid is selected from the group consisting of PG, PS, PA, PI, EPG, EPS, EPA, EPI, SPG, SPE, SPS, SPA, SPI, DPPG, DOPG, DMPG, DSPG, PSPG, DPPS, DOPS, DMPS, DSPS, DPPA, DOPA, DMPA, DSPA, DPPI, DOPI, DMPI, DSPI and a hydrophilic polymer with a long chain of highly hydrated flexible neutral polymer attached to a phospholipid molecule. Examples of the hydrophilic polymer include, but are not limited to, polyethylene glycol (PEG) with a molecular weight about 2,000 to about 5,000 daltons, methoxy PEG (mPEG), ganglioside $GM_1$, polysialic acid, polylactic acid (also termed polylactide), polyglycolic acid (also termed polyglycolide), polylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

In one embodiment, the lipid mixture further comprises a sterol. Sterol used in the present disclosure is not particularly limited, but examples thereof include cholesterol, phytosterol (sitosterol, stigmasterol, fucosterol, spinasterol, brassicasterol, and the like), ergosterol, cholestanone, cholestenone, coprostenol, cholesteryl-2'-hydroxyethyl ether, and cholesteryl-4'-hydroxybutyl ether. The sterol component of the lipid mixture, when present, can be any of those sterols conventionally used in the field of liposome, lipid vesicle or lipid particle preparation. In another embodiment, the lipid mixture comprises of about 10% to about 33% of cholesterol, about 15 to less than about 30 mole % of cholesterol, about 18 to about 28 mole % of cholesterol or about 20 to about 25 mole % of cholesterol.

In an exemplary embodiment, the lipid mixture comprises the first phospholipid, the second phospholipid and the sterol at a mole percent of 29.5% to 90%:3% to 37.5%:10% to 33%.

In further embodiments, the first phospholipid is DOPC, POPC, SPC, or EPC and the second phospholipid is PEG-DSPE or DOPG.

In one embodiment, the lipid mixture is free of fatty acid or cationic lipid (i.e. a lipid carrying a net positive charge a physiological pH).

In some embodiments, the lipid mixture may further comprise a lipid-conjugate of an antibody or a peptide that acts as a targeting moiety to enable liposomes thereof to specifically bind to a target cell bearing a target molecule. Non-limiting examples of the target molecules include, but are not limited to, TNF-α and B cell surface antigen, such as CD20. Other antigens, such as CD19, HER-3, GD2, Gp75, CS1 protein, mesothelin, cMyc, CD22, CD4, CD44, CD45, CD28, CD3, CD123, CD138, CD52, CD56, CD74, CD30, Gp75, CD38, CD33, GD2, VEGF, or TGF may also be used.

The liposomes prepared in this disclosure can be generated by conventional techniques used to prepare vesicles. These techniques include the ether injection method (Deamer et al., Acad. Sci. (1978) 308: 250), the surfactant method (Brunner et al., Biochim. Biophys. Acta (1976) 455: 322), the freeze-thaw method (Pick et al., Arch. Biochim. Biophys. (1981) 212: 186), the reverse-phase evaporation method (Szoka et al., Biochim. Biophys. Acta. (1980) 601: 559 71), the ultrasonic treatment method (Huang et al., Biochemistry (1969) 8: 344), the ethanol injection method (Kremer et al., Biochemistry (1977) 16: 3932), the extrusion method (Hope et al., Biochim. Biophys. Acta (1985) 812:55 65), the French press method (Barenholz et al., FEBS Lett.

(1979) 99: 210) and methods detailed in Szoka, F., Jr., et al., Ann. Rev. Biophys. Bioeng. 9:467 (1980). All of the above processes are basic technologies for the formation of vesicles and these processes are incorporated by reference herein. After sterilization, the pre-formed liposomes are placed aseptically into a container and then lyophilized to form a powder or a cake. In the embodiment where the lipid mixture comprising pre-formed liposomes, said liposomes are obtained by solvent injection method and followed by lyophilization to form the lipid mixture. The lipid mixture comprises one or more bulking agent. In one embodiment, the lipid mixture further comprises one or more buffering agents.

The bulking agents include, but are not limited to, polyols or sugar alcohols such as mannitol, glycerol, sorbitol, dextrose, sucrose, and/or trehalose; amino acids such as histidine, glycine. One preferred bulking agent is mannitol.

The buffering agents include, but are not limited to, sodium phosphate monobasic dihydrate and sodium phosphate dibasic anhydrous.

In the embodiment where the lipid mixture comprises lipids that are not pre-formed into liposomes, the lipid mixture can be prepared by dissolving in a suitable organic solvent, including, but not limited to, ethanol, methanol, t-butyl alcohol, ether and chloroform, and drying by heating, vacuum evaporation, nitrogen evaporation, lyophilization, or other conventional means of solvent removal.

Specific examples of lipid mixture preparation in support of the present disclosure will be described below.

Therapeutic Agent

A therapeutic agent can be a steroid, a nonsteroidal anti-inflammatory drug (NSAID) such as indomethacin, a disease-modifying anti-rheumatic drug (DMARD) or a combination of two or more of the foregoing, as well as a combination of one or more of the foregoing with other ingredients or compounds not specifically listed in this document. DMARDs include small molecule agents, such as methotrexate, leflunomide, sulfasalazine, cyclophosphamide, azathioprine, cyclosporin A, d-penicillamine, antimalarial drugs (e.g. hydroxychloroquine). DMARDs also include biological substances, such as Tumor necrosis factor α (TNF-α) antagonist (e.g. etanercept, trade name Enbrel, commercial available from Wyeth Pharmaceuticals, Inc., Collegeville, USA, Adalimumab, trade name HUMIRA, commercial available from Abbott Laboratories, Abbott Park, Illinois, USA), interleukin-1 receptor antagonist, interleukin-6 receptor antagonist, anti-CD20 monoclonal antibody, CTLA-4-Ig, RGD peptide and the like.

In one exemplary embodiment, the therapeutic agent is a substantially water soluble steroid, such as dexamethasone sodium phosphate (DSP), in a form of solution. In another exemplary embodiment, the therapeutic agent is a substantially water soluble NSAID, such as an acceptable salt of indomethacin. In yet another exemplary embodiment, the therapeutic agent is a substantially water soluble DMARD, such as an acceptable salt of methotrexate, or an TNF-α antagonist. In yet another exemplary embodiment, the therapeutic agent is not covalently bond to a phospholipid or a fatty acid, such as palmitate.

The therapeutic agent of the preset disclosure can be mixed either in ddH$_2$O or a suitable buffer as a solution containing the therapeutic agent for suspending the lipid mixture to obtaine the pharmaceutical composition according to the present disclosure. In some embodiments, the therapeutic agent is not covalently bound to a lipid such as phospholipid or a fatty acid, such as palmitate.

Therapeutic agent or agents can be combined with pharmaceutically acceptable excipients and other ingredients suitable for pharmaceutical formulations (which include formulations for human and animal use, and formulations for research, experimental and related uses). In some embodiments, a citrate buffer is used, preferably sodium citrate. In other embodiments, a chelating agent is used, preferably EDTA.

The therapeutic agent in the pharmaceutical composition described herein includes a therapeutic agent suitable for articular injection or a pharmaceutically acceptable salt thereof. In one embodiment, the therapeutic agent is suitable for intra-articular (IA) injection. Intra-articular injection involves the following steps: 1) identifying and mark an appropriate injection site of the joint to be treated; 2) sterilizing the injection site using aseptic technique and optionally provide local anesthetic; 3) inserting the needle at the injection site into the joint space; and 4) Injecting the medication into the join space. In some embodiments, the needle insertion can optionally be performed under ultrasound guidance. A small amount of synovial fluid is aspirated to confirm that the tip of the needle is within the joint space.

The steroid useful in the present disclosure includes any naturally occurring steroid hormones, synthetic steroids and their derivatives. Examples of the steroid include, but are not limited to, cortisone, hydrocortisone, hydrocortisone acetate, tixocortol pivalate, fluocinolone, prednisolone, methylprednisolone, prednisone, triamcinolone acetonide, triamcinolone, mometasone, amcinonide, budesonide, desonide, fluocinonide, fluocinolone acetonide, halcinonide, betamethasone, betamethasone sodium phosphate, dexamethasone, dexamethasone sodium phosphate (DSP), fluocortolone, hydrocortisone-17-butyrate, hydrocortisone-17-valerate, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, difluprednate, loteprednol, fluorometholone, medrysone rimexolone, beclomethasone, cloprednol, cortivazol, deoxycortone, difluorocortolone, fluclorolone, fluorocortisone, flumethasone, flunisolide, fluorocortolone, flurandrenolone, meprednisone, methylprednisolone, paramethasone or a mixture thereof. In an exemplary embodiment, the steroid is a water soluble steroid. Water soluble steroids include any naturally occurring steroid hormones, synthetic steroids and their derivatives. Water soluble steroids include, but are not limited to, cortisone, hydrocortisone, prednisolone, methylprednisolone, prednisone, DSP, hydrocortisone-17-valerate, fluorocortisone, fludrocortisone, methylprednisolone, paramethasone and plerenone. In one example about 2 to about 100 mg/mL, about 4 to about 80 mg/mL, about 5 to about 60 mg/mL, about 6 to about 40 mg/mL, about 8 to about 20 mg/mL, about 10 to about 16 mg/mL of DSP solution can be used as the solution containing the therapeutic agent as mention above to reconstitute the lipid mixture in a form of cake to obtain the pharmaceutical composition of the present disclosure. In another exemplary embodiment, the steroid is selected from the Group B and Group C steroids according to Coopman Classification (S. Coopman et al., "Identification of cross-reaction patterns in allergic contact dermatitis from topical corticosteroids" Br J Dermatol. 1989 July; 121(1):27-34).

The pharmaceutically acceptable salts of the therapeutic agent include non-toxic salts formed from non-toxic inorganic or organic bases. For example, non-toxic salts can be formed with inorganic bases such as an alkali or alkaline earth metal hydroxide, e.g., potassium, sodium, lithium, calcium, or magnesium; and with organic bases such as an amine and the like.

The pharmaceutically acceptable salts of the therapeutic agent also include non-toxic salts formed from non-toxic inorganic or organic acids. Example of organic and inorganic acids are, for example, hydrochloric, sulfuric, phosphoric, acetic, succinic, citric, lactic, maleic, fumaric, palmitic, cholic, pamoic, mucic, D-glutamic, glutaric, glycolic, phthalic, tartaric, lauric, stearic, salicylic, sorbic, benzoic acids and the like.

The therapeutic agent can be administered at an effective amount by articular injection to reduce the symptoms or signs of arthritis. In one embodiment, the therapeutic agent refers to a steroid, particularly an intra-articular corticosteroid, (such as corticosteroids including, but not limited to, hydrocortisone acetate, methylprednisolone acetate, dexamethasone sodium acetate, betamethasone acetate, prednisolone, triamicinolone acetonide, triamcinolone hexacetonide) which may be administered at a dose ranging from about 0.1 mg to about 300 mg, from about 0.1 mg to about 100 mg, from about 0.1 mg to about 20 mg, from about 0.1 mg to about 18 mg, from about 1 mg to about 300 mg, from about 1 mg to about 100 mg, from about 1 mg to about 20 mg, from about 1 mg to about 18 mg, from about 4 mg to about 300 mg, from about 4 mg to about 100 mg, from about 4 mg to about 20 mg, from about 4 mg to about 18 mg, from about 6 mg to about 18 mg, from about 6 mg to about 16 mg, from about 8 mg to about 16 mg, from about 6 mg to about 12 mg, from about 6 mg to about 16 mg per mL of pharmaceutical composition.

Effective dosages of the therapeutic agent in human may be higher than a recommended or standard dosage known in the art; for example, see *The Orthopaedic Journal of Sports Medicine*, 3(5), 2325967115581163 (DOI: 10.1177/2325967115581163), which is incorporated by reference herein. For example, while the recommended effective and tolerable dosage of triamcinolone hexacetonide as the therapeutic agent is 20 mg, the dosage of the therapeutic agent in the present compositions and methods may be at least 20 mg or higher.

The dosage of the therapeutic agent administered will also depend on the severity of the condition being treated, the particular formulation, and other clinical factors such as weight and the general condition of the recipient and severity of the side effect.

Use of the Pharmaceutical Composition

The pharmaceutical composition may be administered in a single dose treatment or in multiple dose treatments, over a period of time appropriate to the condition being treated. The pharmaceutical composition may conveniently be administered at appropriate intervals, for example, once over a period of a week, a fortnight, six weeks, a month, two months, at least 3 months, at least 6 months or until the symptoms and signs of the condition (i.e. joint pain) resolved.

In a groups of embodiments, the multiple dose treatment by at least two articular injections are administered at a dosing interval selected from the group consisting of two weeks, three weeks, four weeks, five weeks, six weeks, seven weeks, eight weeks, night weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks and twenty-three weeks.

In some embodiments, the pharmaceutical composition is administered at an amount ranging from about 0.5 mL to about 1.5 mL, about 0.6 mL to about 1.2 mL, about 0.8 mL to about 1.2 mL, or about 1.0 mL per articular injection.

The Method of Treating Joint Pain

One aspect of this disclosure is directed to a method of treating joint pain in a subject, comprising the administration an effective amount of the pharmaceutical composition as described herein to the subject in need thereof, whereby the side effects induced by the therapeutic agent are reduced compared to the side effects in a subject following the administration of an immediate release or standard therapeutic agent formulation and/or the efficacy and the release rate of the therapeutic agent of the pharmaceutical composition is increased compared to the efficacy and the release rate of a pharmaceutical composition with more than about 150 µmol of phospholipid per each ml of the pharmaceutical composition. In one embodiment, the subject has arthritis such as osteoarthritis, rheumatoid arthritis, acute gouty arthritis, psoriatic arthritis, reactive arthritis, arthritis due to Ehlers-Danlos Syndrome, haemochromatosis, hepatitis, Lyme disease, Sjogren's disease, Hashimoto's thyroiditis, celiac disease, non-celiac gluten sensitivity, inflammatory bowel disease, Henoch-Schönlein purpura, Hyperimmunoglobulinemia D with recurrent fever, sarcoidosis, Whipple's disease, TNF receptor associated periodic syndrome, Granulomatosis with polyangiitis, familial Mediterranean fever, or systemic lupus erythematosus.

The efficacy refers to the ability of the therapeutic agent to induce a favorable clinical response in a disease. The efficacy also refers to the reduction of clinical sign, such as joint pain, tenderness, transient morning stiffness, and crepitus on joint motion that leads to instability and physical disability. In one embodiment, the efficacy of the therapeutic agent is determined by WOMAC OA index, VAS score or the like. In some embodiments, the sustained, steady state release of the therapeutic agent from the pharmaceutical composition described herein will not induce side effects include, but are not limited to articular cartilage damage or destruction, such as chondrocyte apoptosis, proteoglycan loss, cysts in articular cartilage, articular cartilage degradation or joint destruction. The reduction in side effects in a subject described herein can range from 1%, 5%, 10%, 20%, 30%, 40%, 50%, 60%, 70%, 80%, 90% or 100% when compared with a subject injected with the therapeutic agent not formulated with the pharmaceutical compositions described herein, e.g., without a lipid mixture. This is unexpected as it is well known that exposure to the therapeutic agent, such as triamcinolone acetate (TCA), causes articular cartilage damage or destruction.

The pharmaceutical composition provided herein can be used in combination with any of a variety of additional chemical entities, including but not limited to, analgesics (e.g., bupivacaine, ropivacaine, or lidocaine) or hyaluronic acid preparations (e.g., Synvisc One). In some embodiments, the claimed pharmaceutical composition and additional chemical entities are formulated into a single therapeutic composition, and the claimed pharmaceutical composition and the additional chemical entities are administered simultaneously. Alternatively, the claimed pharmaceutical composition and the additional chemical entities are separate from each other, e.g., each is formulated into a separate therapeutic composition, and the claimed pharmaceutical composition and the additional chemical entities are administered simultaneously, or at different times during a treatment regimen by the same route or different routes, as a single dose or multiple doses.

The following examples further illustrate the present disclosure. These examples are intended merely to be illustrative of the present disclosure and are not to be construed as being limiting.

Example 1: Preparation of a Lipid Mixture

The lipids, including DOPC, DOPG and cholesterol, were combined at a mole percentage of 67.5:7.5:25 and dissolved in 99.9% ethanol at about 40° C. in a flask to form a lipid solution. A tabletop ultrasonic bath was used for lipid dissolution.

The dissolved lipid solution was added to 1.0 mM sodium phosphate solution at 100 mL/min by a peristaltic pump to form a pro-liposome suspension. The pro-liposome suspension was then passed 6 to 10 times through a polycarbonate membrane with a pore size of 0.2 μm. A liposome mixture was obtained and the liposomes had an average vesicle diameter of about 120-140 nm (measured by Malvern Zeta-Sizer Nano ZS-90, Malvern Instruments Ltd, Worcestershire, UK).

The liposome mixture was dialyzed and concentrated by a tangential flow filtration system with Millipore Pellicon 2 Mini Ultrafiltration Module Biomax-100C (0.1 m$^2$) (Millipore Corporation, Billerica, Mass., USA) and then sterilized using a 0.2 μm sterile filter.

The lipid concentration of the filtered liposome mixture was quantified by phosphorous assay and the filtered liposome mixture was formulated with mannitol at a concentration of 2% mannitol and then sterilized again using a 0.2 μm sterile filter. The sterilized liposome mixture was then subject to lyophilization to obtain a lipid mixture in a form of cake.

Example 2: Preparation of a Pharmaceutical Composition

A pharmaceutical composition in accordance with the present disclosure was prepared by mixing the lipid mixture described in Example 1 with a DSP solution, which comprises 13.2 mg/ml dexamethasone sodium phosphate (DSP) ($C_{22}H_{28}FNa_2O_8P$; molecular weight: 516.41 g/L) and 4 mg/ml sodium citrate as DSP pharmaceutical composition used hereafter, whereby each mL of the pharmaceutical composition included about 12.0 mg/mL of DSP and 90 μmol of phospholipid.

Example 3. Controlled Release of the Pharmaceutical Composition

An in vitro release study with a Phase II dose-ranging clinical setting was conducted, pharmaceutical compositions of Example 2 with different doses of DSP were injected into human synthetic synovial fluid (hsSF) and the amount of DSP released was measured at different time points.

Human Synthetic Synovial Fluids (hsSF)

The composition of human synthetic synovial fluid was listed in Table 1. Briefly, the bovine serum albumin (BSA) was dissolved with 0.9% normal saline to a concentration of 30 mg/mL. 1% of Hyaluronic acid (HA, Mw=1.35×10$^6$ Da) was added to the BSA solution and the mixture was gently stirred at room temperature for 2 hours, to ensure complete dissolution of HA. The pH of the solution is 7.3. The human synthetic synovial fluids were contained 0.2% sodium azide to inhibit bacterial growth.

TABLE 1

| Human synthetic synovial fluid (hsSF) | | | |
|---|---|---|---|
| Material | HA (1.35 ×10$^6$ Da) | BSA | 0.9 % normal saline |
| Qty (unit: g) | 1 | 3 | 96 |

In Vitro Release of DSP Pharmaceutical Compositions

The release of DSP from liposomes of the DSP pharmaceutical composition was measured by detecting the changes in entrapment efficiency change at different time intervals. Briefly, various amounts of the DSP pharmaceutical composition was suspended with synthetic synovial fluids at a given temperature (37° C.) and stirred with a stirring bar at 150 rpm (Table 2). At appropriate time intervals, the suspension was collected and free DSP was collected by eluting the suspension through the SPE column, following the procedures as described below for measurement of entrapment efficiency.

TABLE 2

| Group no. | DSP Pharmaceutical composition (12 mg/mL of DSP) | | Synthetic synovial fluid (mL) |
|---|---|---|---|
| | mL | DSP amounts (mg) | |
| 1 | 2 | 24 | 7 |
| 2 | 1.5 | 18 | |
| 3 | 1 | 12 | |
| 4 | 0.67 | 8 | |
| 5 | 0.5 | 6 | |

Entrapment Efficiency

The absorbance intensity of the entrapment efficiency of the collected samples was determined after separating free DSP from the liposomes using SPE cartridge. The SPE column was prepared for use by wetting it with 1 mL methanol followed by 1 mL of distilled water. The column was then equilibrated with 1 mL of normal saline prior to loading the collected suspensions. After loading the suspensions, the SPE column was washed with 3 mL of distilled water, and the free DSP was eluted with 2 mL of elution buffer (containing 2M NH$_4$OAc/MeOH/ACN=2/9/9 (v/v)). The eluted fraction containing the free DSP was monitored using a UV-vis spectrophotometer at 240 nm. The entrapment efficiency (%) was calculated as [1−(Ifree/12)]×100, in which 12 is the theoretical value (mg/mL) of DSP in sample solution, and Ifree is the free DSP concentration.

The data shows that adjustment of phospholipid amount could control release of DSP (Table 3 and FIG. 1). Without wishing to be bound to any theory, it is believed that a relatively high dose of DSP with a high amount of lipids in the pharmaceutical composition (composition No. 5 in Table 3) causes a slow release of small amounts of DSP into the joint environment, while a lower dose of DSP with a lower amount of lipids cannot produce enough sustainable level of free DSP over time. Together with the observation from the below Phase II dose-ranging clinical trial, a pharmaceutical composition with a suitable amount of phospholipids in the pharmaceutical composition is considered to be desired for controlled release of a therapeutic agent for use in treating joint pain. On the basis of the volume of synovial fluid generally ranges from 1 mL to 70 mL, the practical phospholipid concentration per each ml of pharmaceutical composition ranges from 20 μmol to 150 μmol to achieve a desired effective lipid concentration around 90 μmol per 7 mL synovial fluid.

TABLE 3

In vitro release profile of the pharmaceutical composition according to the present application

| No. | Total Phospholipids (μmol) | Total DSP (mg) | Phospholipid concentration in Human synthetic synovial fluids (mM) | Release of DSP from Liposome (percentage) | | | Release of DSP from Liposome (mg/mL) | | |
|---|---|---|---|---|---|---|---|---|---|
| | | | | Day 0 | Day 1 | Day 3 | Day 0 | Day 1 | Day 3 |
| 5 | 180.62 | 24 | 20.07 | 0.0% | 0.0% | −0.7% | 0.000 | 0.000 | −0.019 |
| 4 | 135.47 | 18 | 15.94 | 0.0% | −0.4% | 1.1% | 0.000 | −0.008 | 0.023 |
| 3 | 90.31 | 12 | 11.29 | 0.0% | 3.0% | 4.4% | 0.000 | 0.045 | 0.067 |
| 2 | 60.51 | 8 | 7.89 | 0.0% | 4.1% | 6.9% | 0.000 | 0.043 | 0.073 |
| 1 | 45.16 | 6 | 6.02 | 0.0% | 7.1% | 13.5% | 0.000 | 0.057 | 0.108 |

Figure 2:
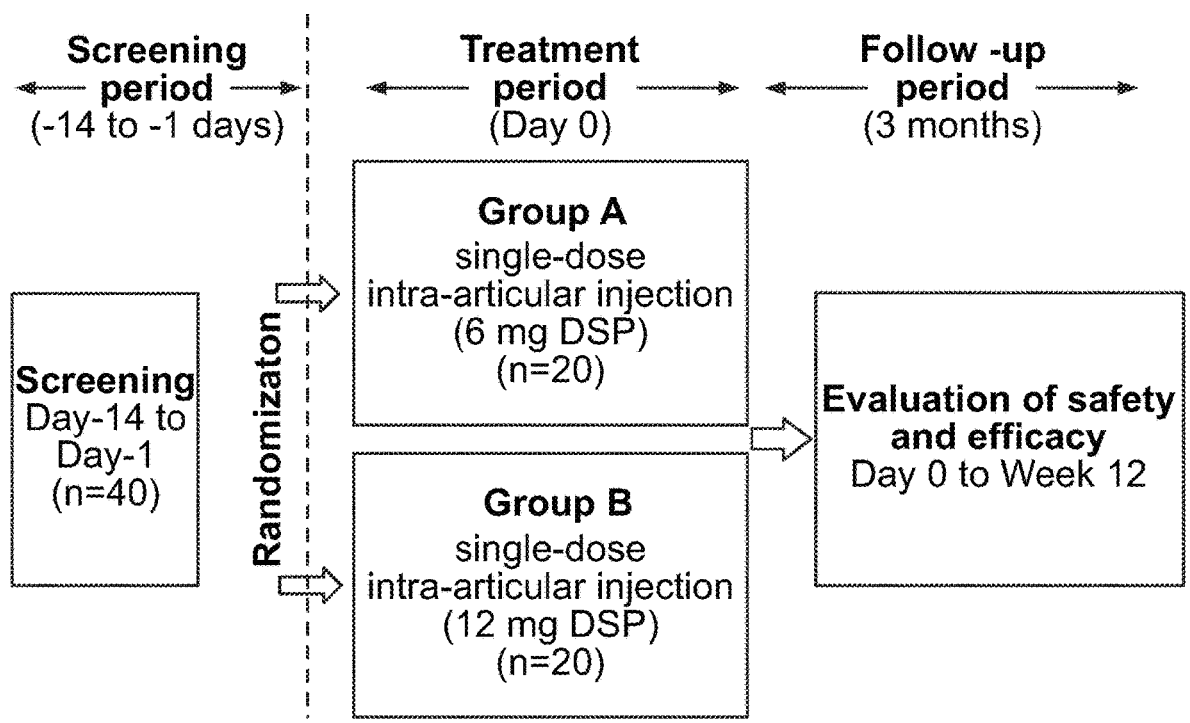
FIG. 2 schematically illustrates the study design.

Example 4. A Randomized, Open-Label Study of Efficacy and Safety of the Dexamethasone Sodium Phosphate (DSP) Pharmaceutical Composition in Patients with Knee Osteoarthritis Method A 12-week randomized, open-label, parallel, and single-dose administration phase I/II trial at 3 study sites in Taipei, Taiwan was conducted. A schematic diagram of the study design is shown in FIG. 2. This study was approved by the local Institutional Review Board of each site before enrolment of any subject at the trial site. This study was performed in accordance with the principles of clinical research guidelines defined in the U.S. 21 CFR Part 312.20, Declaration of Helsinki, and the International Conference on Harmonization of Technical Requirements for Pharmaceuticals for Human Use (ICH) harmonized tripartite guideline regarding Good Clinical Practice. The study protocol was registered at ClinicalTrial.gov (NCT02803307). A written informed consent was obtained from all patients for participation in this trial.

Patients at least 20 years of age and had a documented diagnosis of osteoarthritis (OA) of the knees for at least 6 months prior to the screening visit were recruited in the study. The diagnosis of OA was based on clinical and radiological criteria of American College of Rheumatology Criteria for Classification of Idiopathic OA of the knee (Arthritis Rheum. 1986; 29:1039-49). Additionally, the eligible patients were required to have at least Grade 2 severity in the study knee based on the Kellgren-Lawrence (KL) grading scale (Br J Ind Med. 1952; 9:197-207), a subject-related visual analog scale (VAS) pain score>4 at baseline, and the ability to understand the study protocol and the agreement to participate. Patients were excluded if they have used systemic corticosteroids for the last 30 days prior to baseline, or NSAIDs, analgesics, or rehabilitation therapy within 7 days prior to baseline; had a history of Reiter's syndrome, systemic lupus erythematosus, Sjogren's syndrome, systemic sclerosis, inflammatory myositis, mixed connective tissue disease, palindromic rheumatism, rheumatoid arthritis, psoriatic arthritis, ankylosing spondylitis, Behçet's disease, arthritis associated with inflammatory bowel disease, sarcoidosis, vasculitis, cryoglobulinemia, or amyloidosis; or had clinical signs and symptoms of acute infection or infection-related inflammation in the other knee before dosing.

A total of 46 patients with knee OA were screened, of whom 40 patients met the inclusion criteria and were randomized into 2 groups. The screening visit was performed within 14 days before the start of the trial. Only 1 knee was selected as the study knee to receive the study drug and undergo subsequent evaluation. Administration of the study drug was discontinued if underlying acute inflammation or infection in the other knee occurred. Eligible subjects were randomized 1:1 to a single dose of the DSP pharmaceutical composition as prepared by the method as described in Example 2 at dose levels of: (1) 6 mg DSP with about 45 μmol phospholipid (Group A) or (2) 12 mg DSP with about 90 μmol phospholipid (Group B). The DSP pharmaceutical composition used in this study were prepared by the method as described in the previous Examples and designed to provide both short (immediate)- and long-acting forms of DSP, after the reconstitution. Each subject was evaluated for 12 weeks following a single intra-articular injection.

The primary objective of this study was to evaluate the safety and tolerability of the two different dose levels of the DSP pharmaceutical compositions. Safety assessments were measured by adverse events (AEs), serious AEs (SAEs), vital signs, changes in physical examination, electrocardiography, and clinical laboratory tests. The secondary objective of the study was to assess the efficacy of the DSP pharmaceutical compositions by measuring the changes in subject- and physician-reported pain scores (VAS), Western Ontario and McMaster Universities (WOMAC) arthritis index score, and Investigator Global Assessment of Response to Therapy (IGART) of the study knee. At Weeks 0, 1, 4, 8, and 12, VAS and WOMAC were assessed. At Weeks 1, 4, 8, and 12, IGART was assessed. Pain score for the study knee was assessed using the VAS scale (ranging from 0 [no pain/tenderness] to 10 [worst pain/tenderness ever]). The WOMAC index included 3 subscales, with score ranging from 0 to 4 for each subscale: pain (5 items), stiffness (2 items), and physical function (17 items). Patient's response to the study drug administration was determined by the investigator in the IGART assessment, with 1 out of 5 ratings (none, poor, fair, good, and excellent) selected at each of the scheduled visit (excluding baseline).

Statistical Analysis

Sample size for this trial was not determined through pre-specified powering assumptions. A total of 40 patients with OA of knee were planned to be enrolled in this trial. All statistical assessments were two-sided and evaluated at a significance level of 0.05. Missing data (including those due to early discontinuations) were not imputed. For continuous endpoints (safety evaluation of plasma cortisol, WOMAC Index, and VAS), descriptive statistics including the number of observation, mean, median, standard deviation, minimum, and maximum were presented for the raw data as well as change from baseline. Also, the continuous variables were analyzed by Wilcoxon Rank Sum Test to compare the difference between the treatment groups, and Wilcoxon signed-rank test was used to compare the change from baseline. For categorical endpoints (IGART, number of patients achieving 30% and 50% or more decrease from baseline in WOMAC and VAS), counts and percentages were used. The Chi-square test was performed to compare the difference between groups, while Fisher's exact test was applied where the data were sparse. All the statistical analyses were conducted using SAS® software, Version 9.3 of the SAS System for Windows 7. In this study, safety population was used for safety analysis, whereas intent-to-treat (ITT) and per-protocol (PP) populations were used for efficacy analysis. The safety population was defined as all subjects who received any dose of the DSP pharmaceutical composition. The ITT population was defined as all subjects who received at least 1 full dose of the DSP pharmaceutical composition and had at least 1 post-baseline efficacy assessment. The PP population was defined as all subjects in the ITT population who did not have any major protocol deviation/violation. All 40 subjects were included in the safety and ITT populations. Thirteen subjects, including 6 subjects in Group A and 7 subjects in Group B, were included in the PP population. The major conclusions were based on the PP population.

Results

Figure 3:
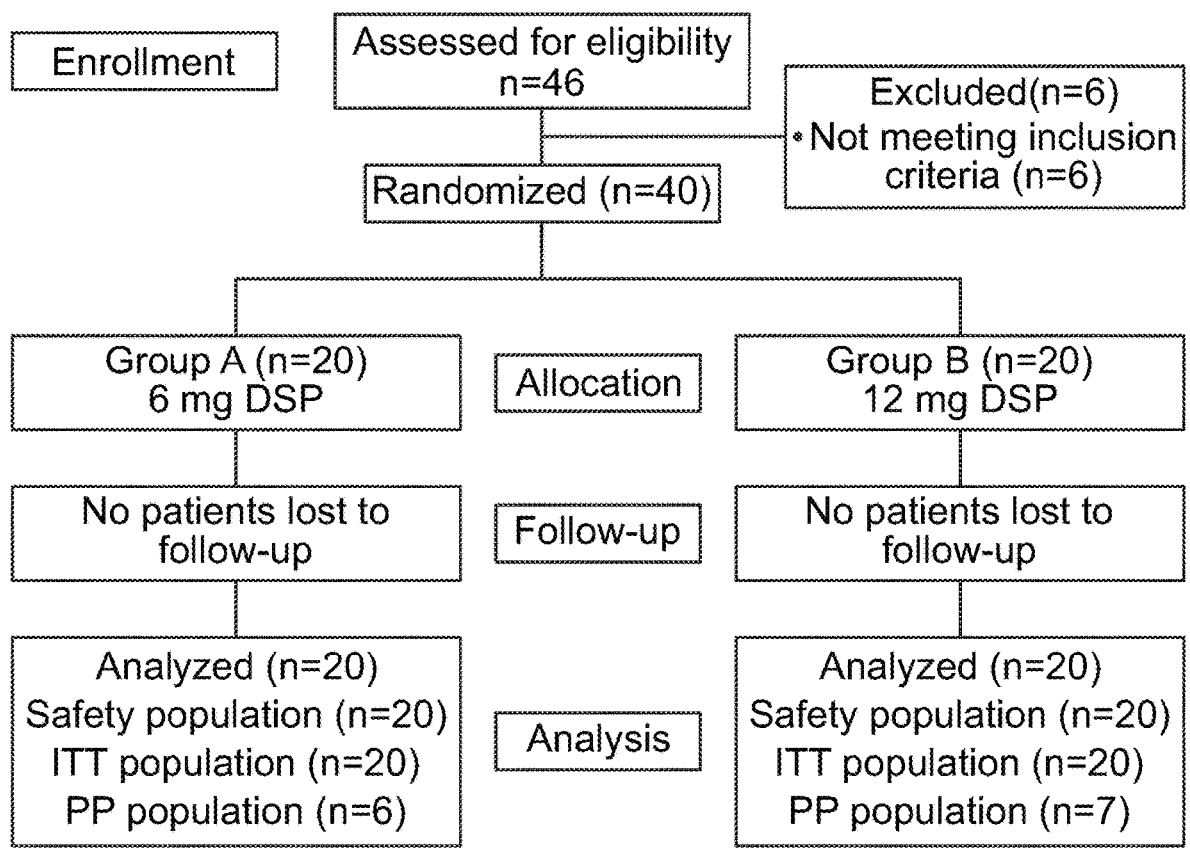
FIG. 3 schematically illustrates the study disposition.

In the present study, a total of 46 subjects were screened, of which 6 were screen failures. Forty subjects were enrolled in the study; out of these, 39 met the eligibility criteria. One subject diagnosed with OA of the knee for less than 6 months prior to the screening visit was enrolled. The subjects were randomly assigned into Group A and Group B of 20 subjects each, receiving 6 mg DSP with 45 μmol phospholipid in the pharmaceutical composition per each intra-articular injection and 12 mg DSP with 90 μmol phospholipid in the pharmaceutical composition per each intra-articular injection, respectively. The summary of subject disposition is shown in FIG. 3 and the demographics information of the study subjects is presented in Table 4.

TABLE 4

Summary results of demographics at baseline

| Variable | Status/Statistics | Safety population Group A (6 mg) (N = 20) | Group B (12 mg) (N = 20) | Total (N = 40) |
|---|---|---|---|---|
| Race | East Asian | 20 (100%) | 20 (100%) | 40 (100%) |
| Age | n | 20 | 20 | 40 |
|  | Mean (SD) | 66.7 (10.04) | 68.10 (8.03) | 67.40 (9) |
|  | Median (min, max) | 67.5 (49, 89) | 69.5 (52, 84) | 68.50 (49, 89) |
| Sex | Male | 2 (10%) | 6 (30%) | 8 (20%) |
|  | Female | 18 (90%) | 14 (70%) | 32 (80%) |
| Was confirmation of osteoarthritis obtained at screening visit? | | | | |
|  | Yes | 20 (100%) | 20 (100%) | 40 (100%) |
|  | No | 0 (0%) | 0 (0%) | 0 (0%) |
| Was the Kellgren-Lawrence (KL) score assessed at screening visit? | | | | |
|  | Yes | 20 (100%) | 20 (100%) | 40 (100%) |
|  | No | 0 (0%) | 0 (0%) | 0 (0%) |
| KL score | | | | |
|  | Grade 0: no radiographic features of osteoarthritis are present | 0 (0%) | 0 (0%) | 0 (0%) |
|  | Grade 1: doubtful joint space narrowing (JSN) and possible osteophytic lipping | 0 (0%) | 0 (0%) | 0 (0%) |

TABLE 4-continued

Summary results of demographics at baseline

| Variable | Status/Statistics | Safety population Group A (6 mg) (N = 20) | Group B (12 mg) (N = 20) | Total (N = 40) |
|---|---|---|---|---|
|  | Grade 2: definite osteophytes and possible JSN on anteroposterior weight-bearing radiograph | 7 (35%) | 5 (25%) | 12 (30%) |
|  | Grade 3: multiple osteophytes, definite JSN, sclerosis, possible bony deformity | 10 (50%) | 10 (50%) | 20 (50%) |
|  | Grade 4: large osteophytes, marked JSN, severe sclerosis and definitely bony deformity | 3 (15%) | 5 (25%) | 8 (20%) |

All the 40 subjects were of East Asian origin. The mean age was 67.4 years and 8 (20%) were males. The subjects were ranked as Grade 2 (n=12), Grade 3 (n=20), and Grade 4 (n=8) on the KL grading scale.

No SAEs, important AEs, or AEs leading to either withdrawal or death occurred in this study. Since long-term use of corticosteroid might lead to elevated blood sugar or even diabetes, change of HbA1c was measured. No statistically significant difference was observed in the mean changes of HbA1c from baseline (Week 0) to Week 12 in either Group A or Group B.

Transient cortisol reduction was a well-described physiologic response in patients who receive IA corticosteroid injections. Mean values of cortisol showed reduction from baseline 1 week after injection but remained in the normal range, and no subjects reported signs or symptoms of adrenal insufficiency.

Figure 4A:
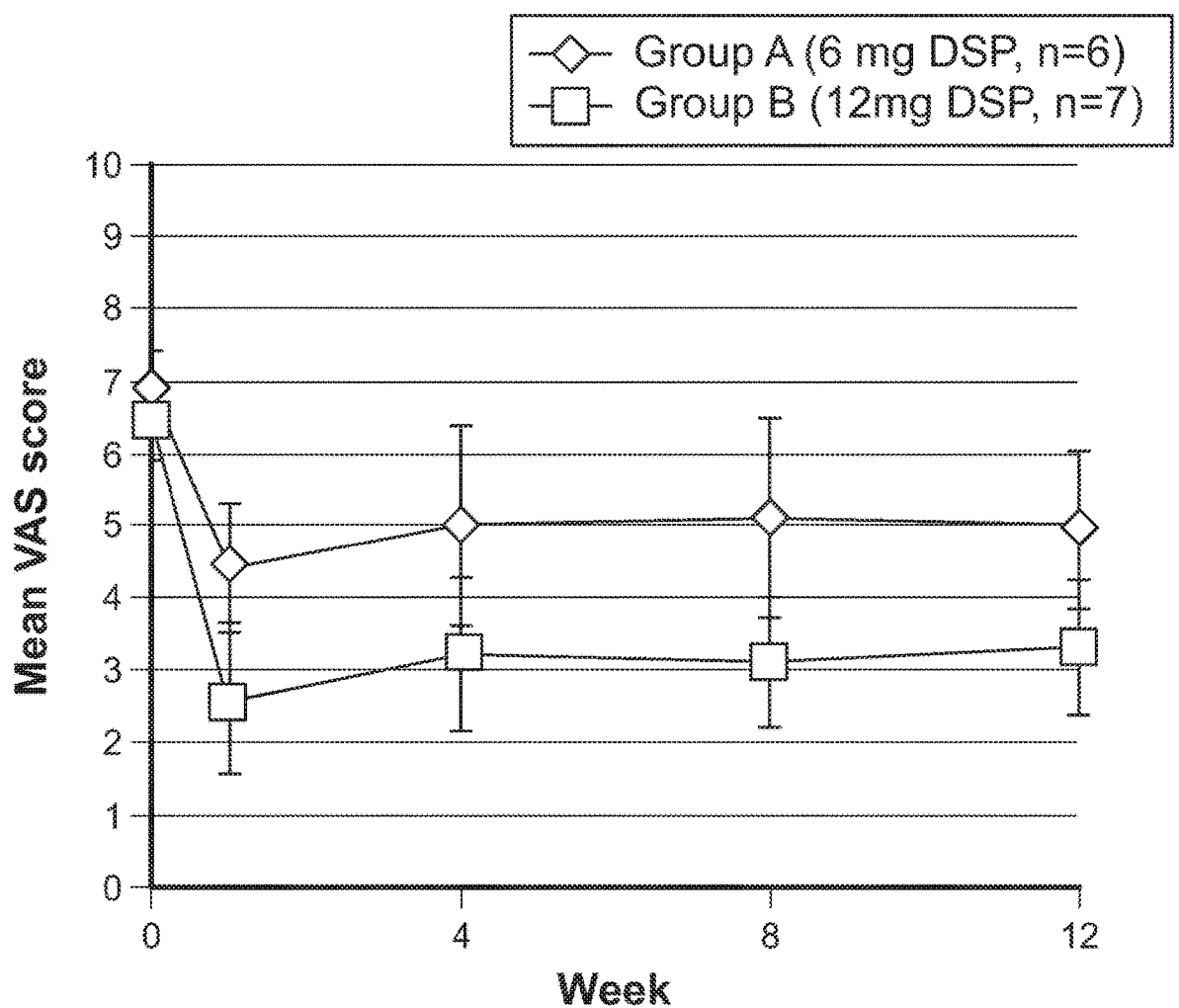
FIG. 4A and FIG. 4B show the subject-related pain VAS score and mean change in subjects receiving 6 mg and 12 mg of DSP in the pharmaceutical compositions of the present disclosure.
Figure 4B:
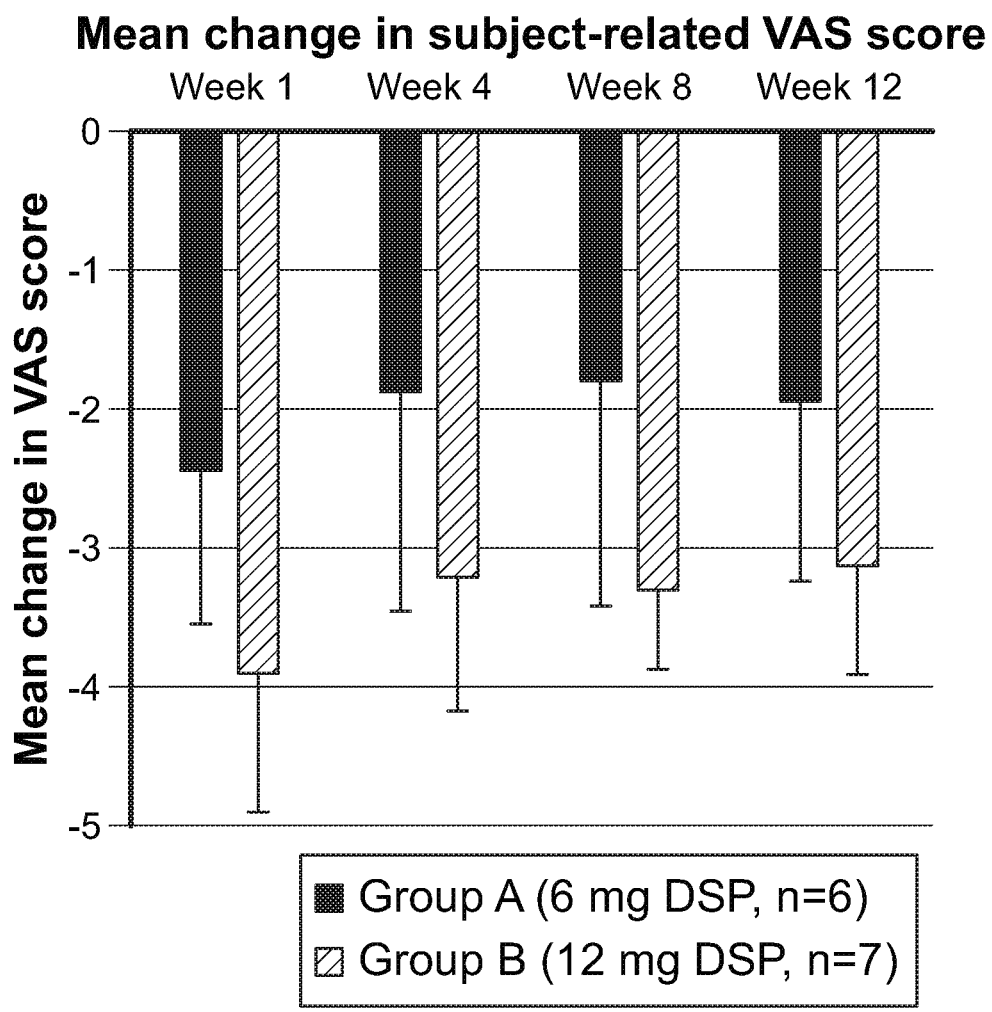
Figure 5A:
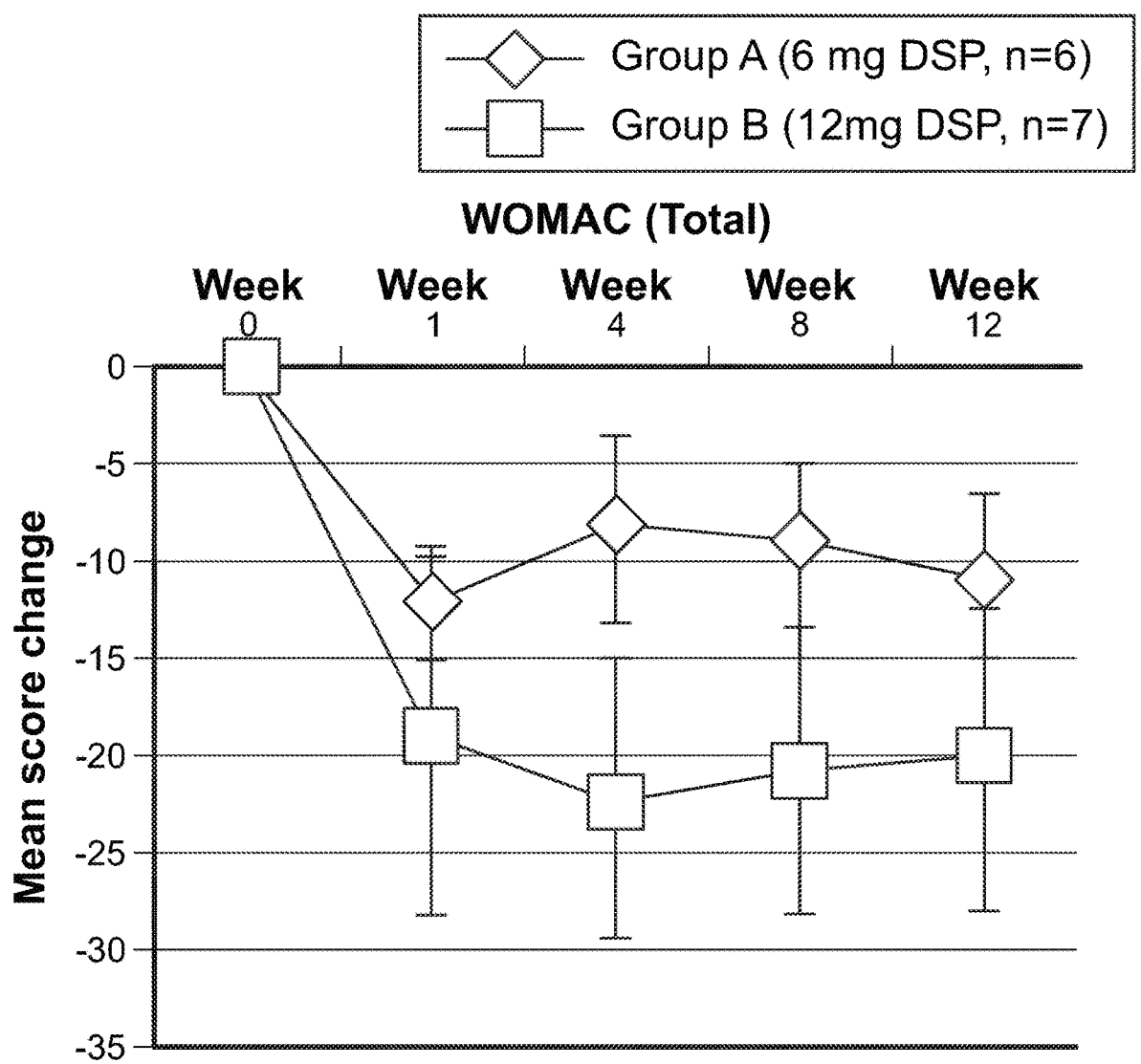
FIG. 5A to FIG. 5D are line graphs showing the mean changes in WOMAC scores in subjects receiving 6 mg and 12 mg of DSP in the pharmaceutical compositions of the present disclosure.
Figure 5B:
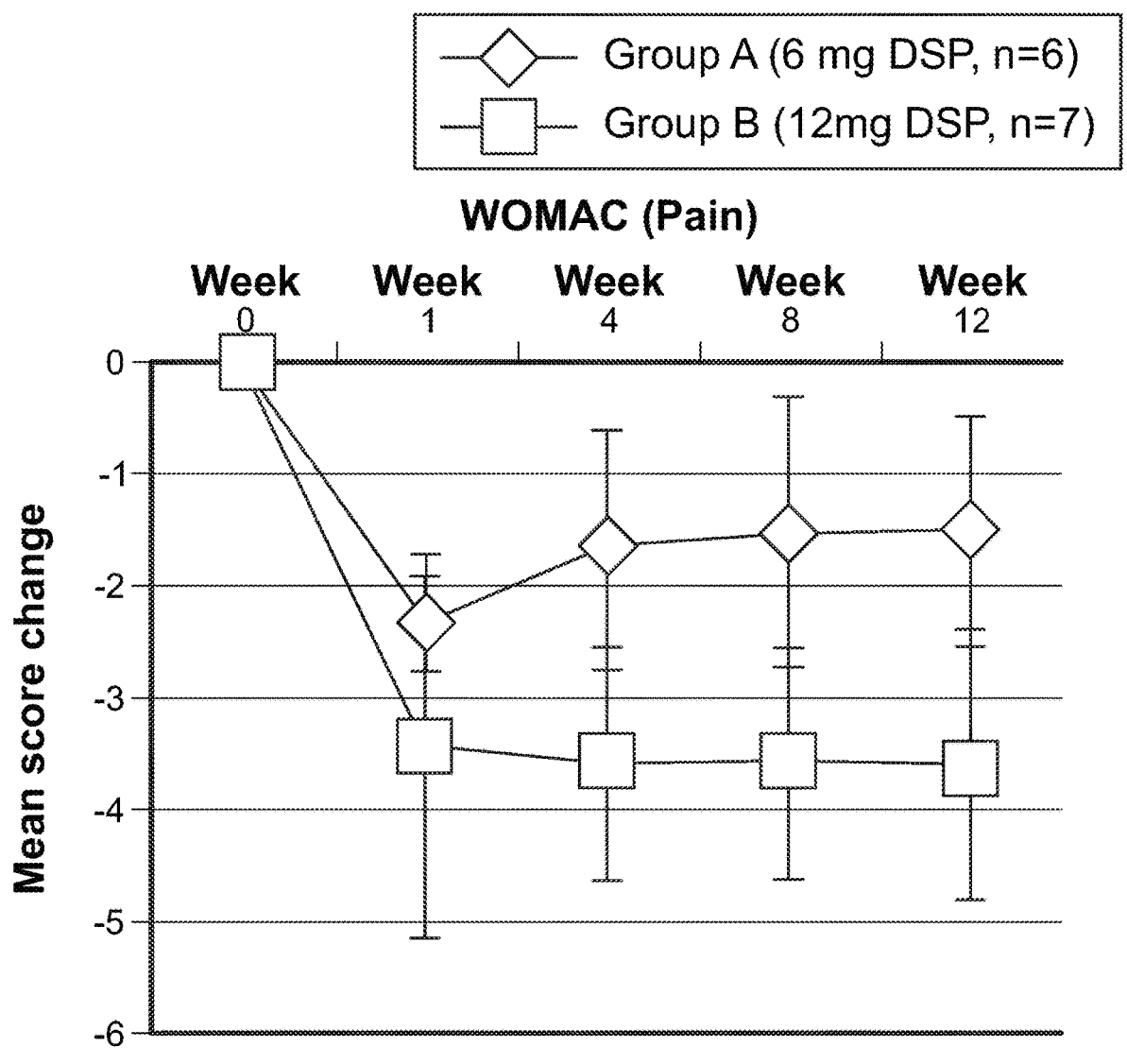
Figure 5C:
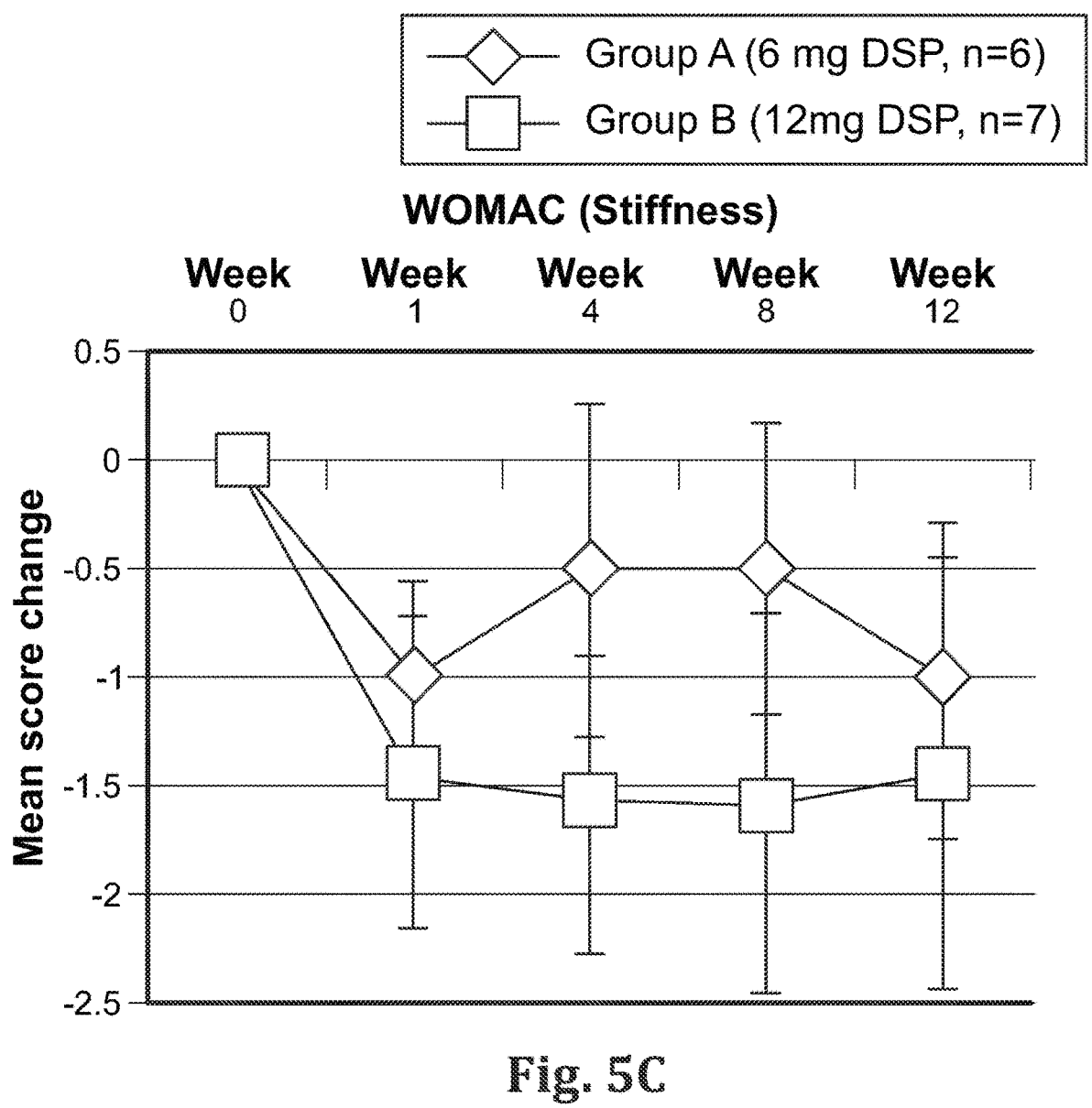
Figure 5D:
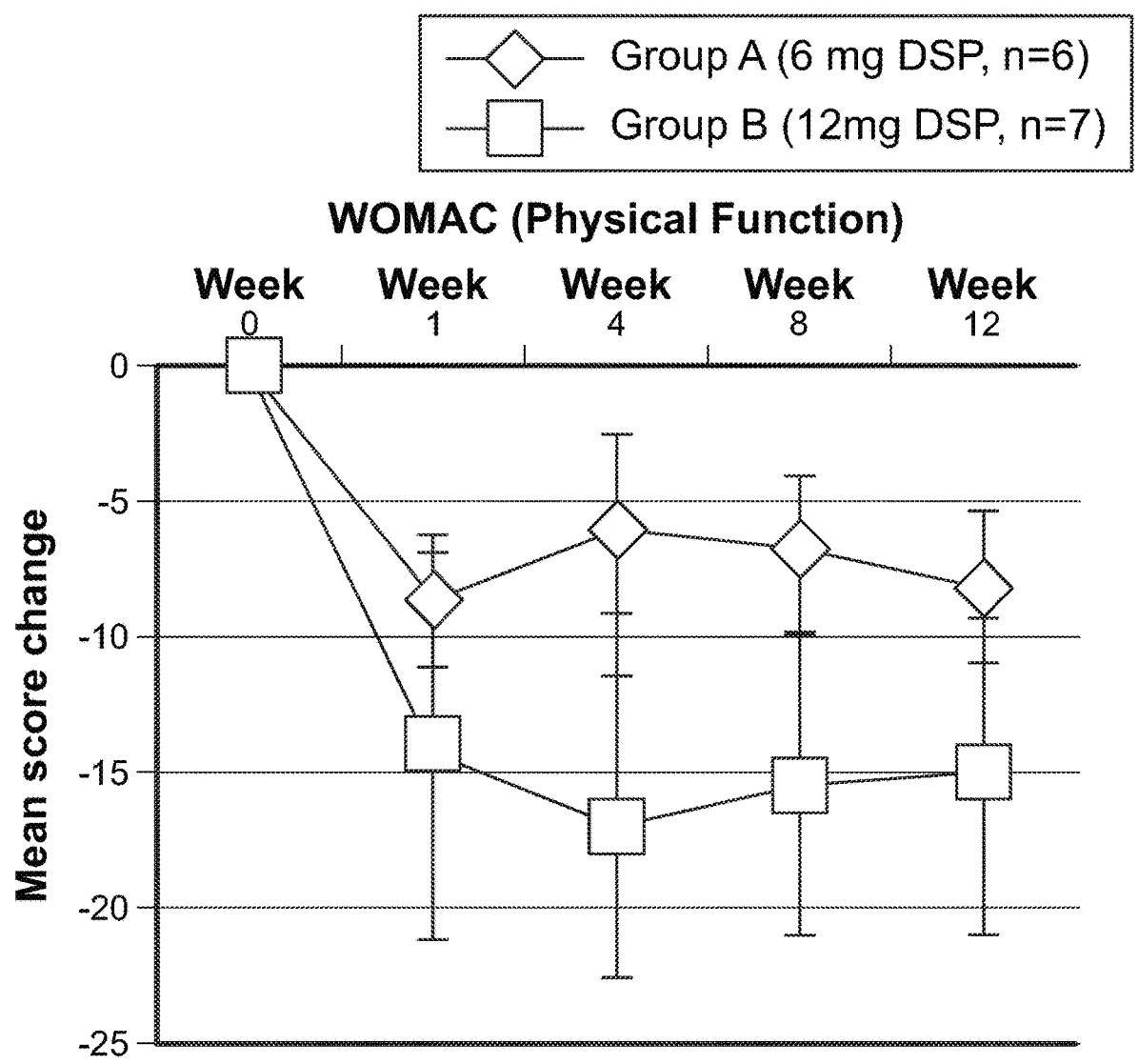

In the PP population, the mean values of subject- and physician-related pain score (VAS) showed sustained decreases from baseline in both Group A and Group B at each scheduled visit through end of study at Week 12 (FIG. 4A and FIG. 4B). The mean changes of subject-related pain score in Group A, from baseline to Weeks 1, 4, 8, and 12 were −2.45, −1.90, −1.80, and −1.95, respectively. In Group B, the mean changes of subject-related pain score from baseline to Weeks 1, 4, 8, and 12 were −3.90, −3.23, −3.33, and −3.14, respectively. Statistical significance ($p<0.05$) was only reached for the mean changes from baseline to each of the scheduled returned visit in Group B. The mean changes of physician-related pain score in Group A, from baseline to Weeks 1, 4, 8, and 12 were −2.95, −4.33, −3.22, and −4.90, respectively. In Group B, the mean changes of physician-related pain score from baseline to Weeks 1, 4, 8, and 12 were −3.41, −3.03, −3.80, and −4.33, respectively. All the mean changes from baseline were statistically significant, except the mean change from baseline to Week 8 in Group A (−3.22±1.78, p=0.0625). Similar trends were also observed in the ITT population.

There was a larger score reduction in the WOMAC pain, stiffness, and physical function subscales from baseline to each scheduled visit observed in Group B compared to Group A (FIGS. 5A to 5D). The mean value of WOMAC total score at baseline (Week 0) in Group A and Group B of the PP population was 37.83±19.90 and 43.29±15.16

(mean±SD), respectively. These values decreased at each visit after the single administration of the study drug in both Group A and Group B. The mean change in WOMAC total score from baseline to Weeks 1, 4, 8, and 12 were −12.17, −8.33, −9.00, and −10.83, respectively, in Group A, and −19.00, −22.29, −20.71, and −20.14, respectively, in Group B. This trend was also observed in the ITT population.

For both the ITT and PP populations, no statistical significance was observed between Group A and Group B in the IGART rating at Weeks 1, 4, 8, and 12. In the PP population (n=13), 33-67% patients' response in Group A and 43-100% patients' response in Group B were rated as good by the investigator from Week 1 through Week 12. In the ITT population (n=20), 50-65% patients' response in Group A and 45-60% patients' response in Group B were rated as good by the investigator from Week 1 through Week 12.

In the current phase I/II trial, intra-articular injection of the DSP pharmaceutical compositions was well tolerated by all subjects with knee OA. Other AEs reported in this study were not related to the treatment, and most of these AEs were mild in severity. No SAEs, important AEs (injection-related local reaction), or AEs leading to either withdrawal or death occurred.

The DSP pharmaceutical compositions did not show any microscopic findings, such as proteoglycan loss, in rabbits and beagle dogs. Single or repeat intra-articular dose administration of the DSP pharmaceutical compositions did not induce any cartilage damage or chondrotoxicity in animal studies, while cartilage damage has been reported with repeated intra-articular injections of free dexamethasone, triamcinolone, and other steroids.

Dexamethasone has shown pain reduction and improvements in arthritis comparable to a long-acting corticosteroid, triamcinolone. This suggests that the DSP pharmaceutical composition with a sustained-release profile is likely to enhance the therapeutic benefit of dexamethasone for a much longer duration than other drugs in the class.

The current phase I/II study was the first trial to administer the DSP pharmaceutical composition with a phospholipid between 20 µmol to 150 µmol per mL or total amount at 80 µmol to 110 µmol in subjects with knee OA as intra-articular injection. The study demonstrated the therapeutic benefit of the 6 mg to 12 mg of DSP pharmaceutical composition for at least 12 weeks, which indicates its longer duration of action than other cortico steroids. A trend of sustained pain relief determined by VAS pain score and symptom relief determined by WOMAC OA index was observed for 12 weeks after receiving a single dose of the DSP pharmaceutical composition.

Example 5. Comparison Analysis of Efficacy of the DSP Pharmaceutical Composition in Patients with Knee Osteoarthritis A multi-center, double-blind, placebo-controlled Phase II clinical trial to explore the safety and treatment efficacy of two different dose levels of the pharmaceutical composition of the present disclosure in patients with knee OA was completed in August 2018. In this clinical trial, 75 patients with a mean age of 63.9 years, moderate degeneration knee OA, and VAS scores of 5-9 were randomized into three different trial groups, each receiving a single intraarticular administration of (a) a pharmaceutical composition comprising 12 mg of DSP and 90 µmol phospholipid (denoted hereafter as TLC599 12 mg), (b) a pharmaceutical composition comprising 18 mg of DSP and 135 µmol phospholipid (denoted hereafter as TLC599 18 mg), or (c) a placebo control (saline) (denoted hereafter as Placebo).

The primary endpoint was to evaluate the mean change from baseline by WOMAC pain scores through Week 12. Other analyses such as change from baseline in WOMAC pain, WOMAC physical function, and VAS scores through and at various time points up to Week 24, as well as the proportion of clinically durable responders, were included in the secondary endpoints. Safety and efficacy were assessed at Day 3, Week 1, and every four weeks up to 24 weeks.

Figure 6:
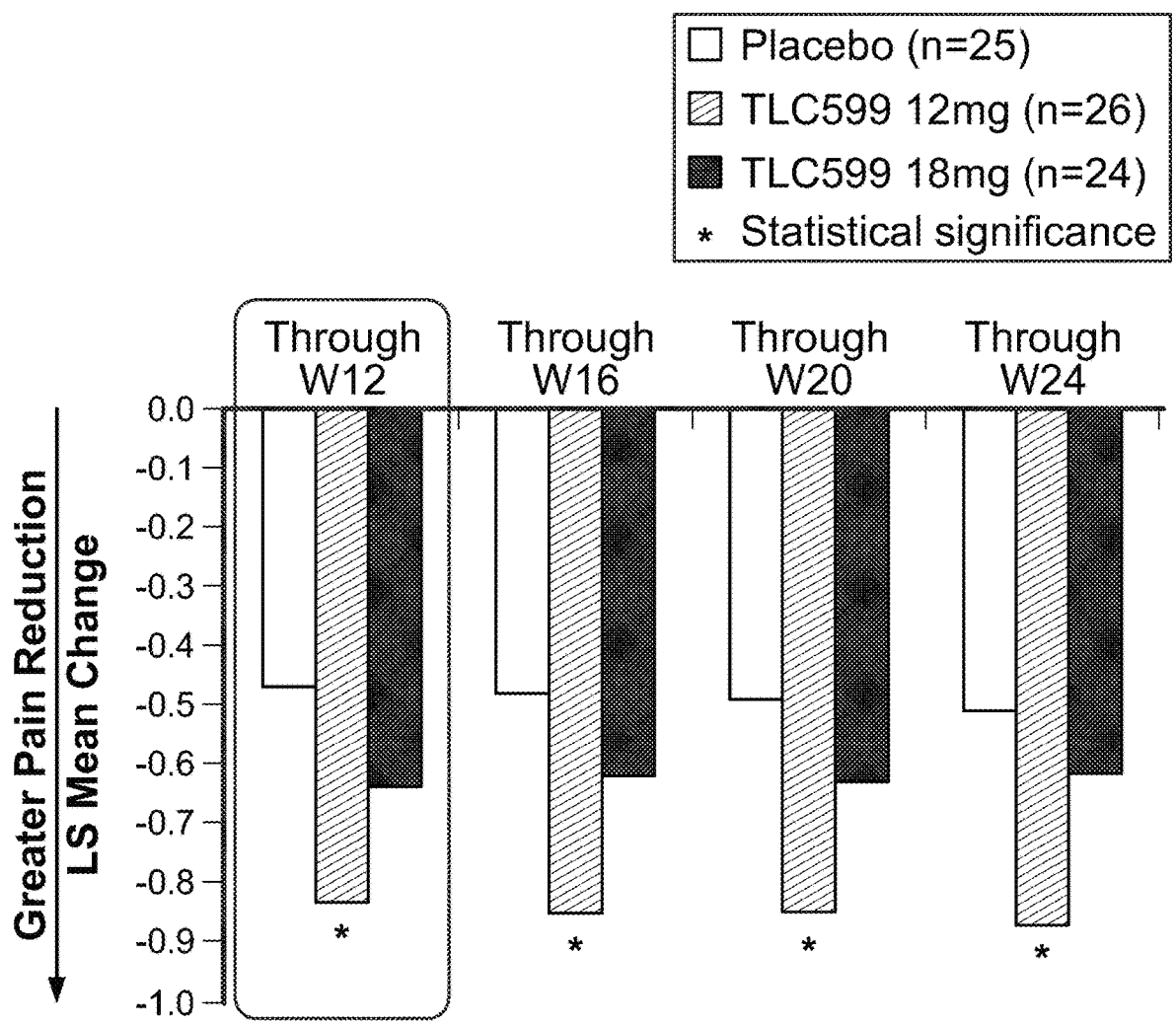
FIG. 6 shows the mean changes in WOMAC scores in subjects receiving 6 mg, 12 mg and 18 mg of DSP in the pharmaceutical compositions of the present disclosure through Week 12 as well as Weeks 16, 20 and 24.

Using the WOMAC pain outcome measure, TLC599 12 mg demonstrated statistically significant improvement in pain relief compared to placebo from Day 3 through Week 12, meeting the primary endpoint. Furthermore, TLC599 12 mg demonstrated persistent and statistically significant improvement in pain relief compared to placebo from Day 3 through Week 16, Week 20, and Week 24, as shown in FIG. 6 and Table 5, reflecting the sustained duration of pain control for at least 24 weeks. TLC599 12 mg also demonstrated statistically significant improvement in pain relief compared to placebo at Week 12, Week 16, Week 20, and Week 24.

TABLE 5

WOMAC pain score of TLC599 12 mg, TLC599 18 mg and Placebo

| Group | Week 12 | Week 16 | Week 20 | Week 24 |
|---|---|---|---|---|
| Placebo | −0.47 | −0.48 | −0.49 | −0.51 |
| TLC599 12 mg (90 µmol phospholipid) | −0.83* (p = 0.0027) | −0.85* (p = 0.0024) | −0.85* (p = 0.0033) | −0.87* (p = 0.0037) |
| TLC599 18 mg (135 µmol phospholipid) | −0.64 (p = 0.0971) | −0.62 ((p = 0.1498) | −0.63 (p = 0.1558) | −0.62 (p = 0.1985) |

LS Mean from MMRM
*p-value <0.05, derived from one-sided test and compared with Placebo Similar results were observed using the WOMAC physical function as outcome measure. Patients treated with TLC599 12 mg displayed significantly greater improvement in WOMAC physical function than placebo from Day 3 through Weeks 12, 16, 20, and 24, as well as at Week 12, 16, 20, and 24 (p<0.05).

Similar results were also observed using the VAS pain scores as outcome measure. TLC599 12 mg demonstrated statistically significant improvement in pain relief compared to placebo from Day 3 through Week 12, Week 16, Week 20, and Week 24, again reflecting the sustained duration of pain control for at least six months. TLC599 12 mg also demonstrated statistically significant improvement in pain relief compared to placebo at Week 12, Week 16, Week 20, and Week 24.

Transient cortisol reduction was a well-described physiologic response in patients who receive IA corticosteroid injections. Thus, the cortisol reduction seen in this study was an expected pharmacodynamic response to IA corticosteroid injection that was closely monitored. Laboratory abnormalities of blood cortisol level were reported as mild in intensity with 2 exceptions (1 moderate cortisol decreased, 1 severe glucocorticoid deficiency). None of these cortisol laboratory events were reported with associated signs or symptoms that might be attributed to hypocortisolism and all were resolved without treatment or sequelae. Most of these events were noted with an onset at the Day 3 time point and of these most were resolved by the next scheduled visit at Week 1".

The amount (approximately 40%) of free dexamethasone in the TLC599 12 mg is slightly above the typical immediate-release DSP dose (4 mg) used for IA injection.

The TEAEs seen in this study were expected in the population studied. TLC599 was generally safe and well tolerated. Additionally, there was a lower incidence of overall TEAEs, drug-related AEs, and cortisol-related AEs in the TLC599 12 mg than in the TLC599 18 mg.

In the current study fasting blood glucose was monitored at each visit. One patient in the TLC599 12 mg group was assessed with TEAEs of blood glucose increased (with 2 separate events, 1 mild and 1 moderate), and another patient in the TLC599 18 mg group with an AE of impaired fasting glucose (mild). Blood glucose increased (both events) was judged not related to study treatment.

Notably, these patients did not display abnormality of HbA1c during the trial. Therefore, any increases in blood glucose were likely transient and mild.

Example 6. Evaluation of Effect of Lipid Content in the DSP Pharmaceutical Composition in Animal Model of Osteoarthritis To evaluate the changes in lipid content as well as interaction among drug and lipid on a pharmaceutical composition suitable for articular delivery in vivo performance, DSP pharmaceutical compositions with high and low lipid amounts were prepared and evaluated for potential effect appearing in indicated conditions as below.

Collagen-type II induced arthritis (CIA) rat model was used to determine the influence of the lipid content of DSP pharmaceutical composition on the therapeutic activity of DSP. A total of 30 Lewis rats was be induced by type II collagen emulsified with Freund's incomplete adjuvant (FIA) on day 1 and then boosted again on day 8 via intradermal tail injection. Clinical visual arthritis scores (Clinical Score) indicating the severity of arthritis was graded using an articular index ranging from 0 to 4 (see table 6). A total score for each rat was calculated by summing the scores for both hind paws with a maximum possible score of 8 for each individual rat. On Day 17, the disease was successfully induced with a total Clinical Visual Arthritis Score of 8, the test articles were administrated to both paws of the rats. DSP pharmaceutical compositions with various amounts of lipid were prepared according to the method as described in Example 2 except that the resultant lipid content of each was as indicated in the below Table 7. Saline and 12 mg/mL dexamethasone phosphate solution in absence of lipid [Dexamethasone Phosphate (DP) Injection] (unformulated drug) were used as control groups.

TABLE 6

The grade of Clinical Visual Arthritis Score

| Severity score | Description |
| --- | --- |
| 0 | No evidence of erythema and swelling |
| 1 | Erythema and mild swelling confined to the tarsus or ankle joint |
| 2 | Erythema and mild swelling extending from the ankle to the tarsus |
| 3 | Erythema and moderate swelling extending from the ankle to metatarsal joints |
| 4 | Erythema and severe swelling encompass the ankle, foot and digits, or ankylosis of the limb |

TABLE 7

The formulations of DSP pharmaceutical compositions with various lipid contents and used controls

| Group number/ Test Article in CIA rat model | Phospholipid content (μmol/mL) | DSP concentration (mg/mL) | Dosage (mg/paw) | Injection volume (mL/paw) |
| --- | --- | --- | --- | --- |
| 1/Saline | — | — | — | 0.05 |
| 2/TLC599CQA_L01 | 119 | 11.5 | 0.6 mg/paw | 0.05 |
| 3/TLC599CQA_L08 | 67 | 12.2 | 1.2 mg/animal | 0.05 |
| 4/TLC599CQA_L09 | 90 | 11.9 | | 0.05 |
| 6/DP Injection | — | 13.2 | | 0.04 |

Figure 7:
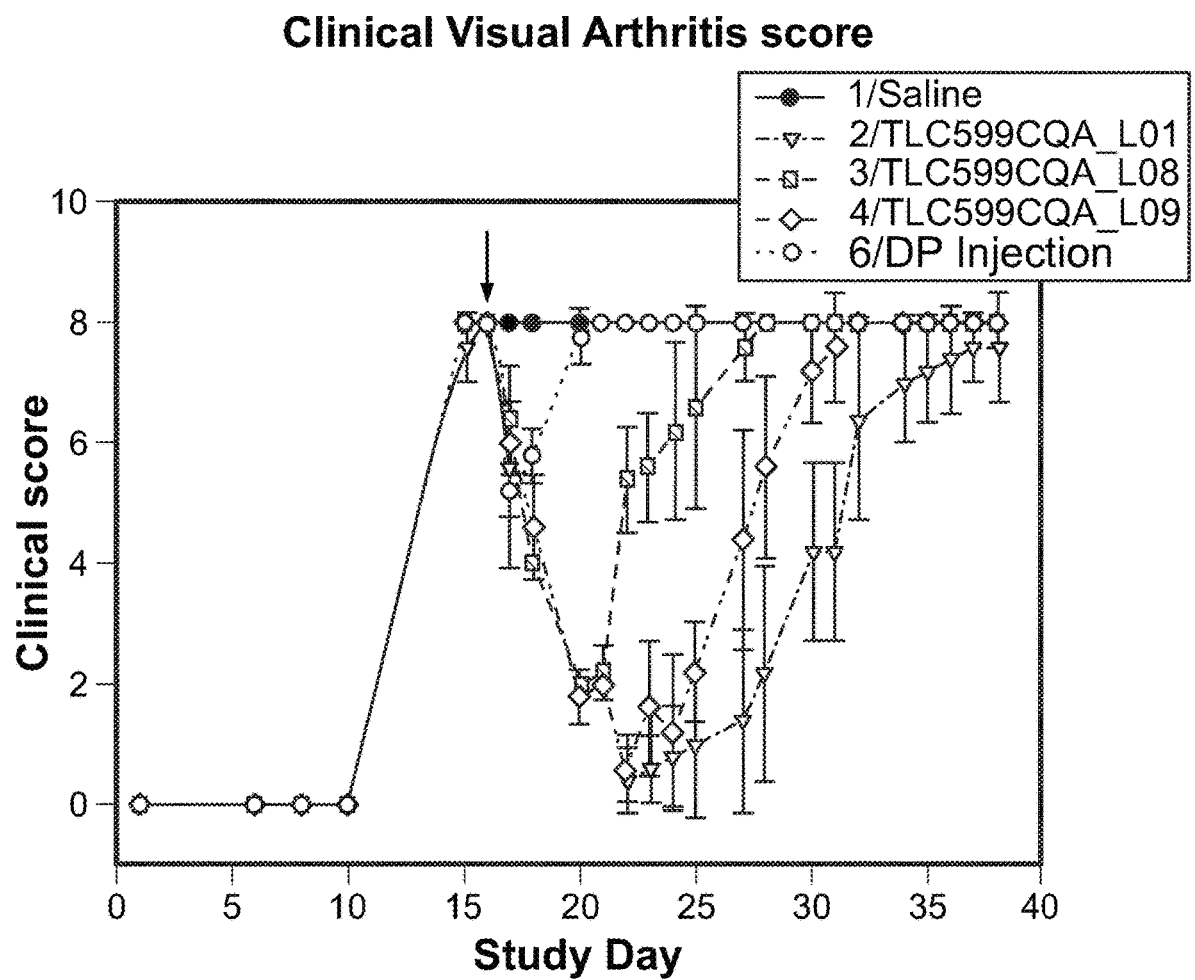
FIG. 7 is a chart of clinical visual arthritis score (VAS) in subjects receiving the pharmaceutical composition of the present disclosure in an animal model and test articles were administered on day 16; and solid arrow indicates the treatment date.

The results showed that the correlation between lipid content in the pharmaceutical compositions suitable for articular delivery and anti-arthritic effectiveness based on the assessment of Clinical Score (FIG. 7).

In vivo efficacy study results reported, regardless of the low or high lipid content (more than 67 μmol phospholipid per mL of DSP pharmaceutical composition) of the TLC599 formulation, the duration of the prolonged efficacy was increased by at least 2.5-fold compared to unformulated drug. However, the longer duration of anti-arthritis was speculated in a range of lipid content (greater than 67 μmol phospholipid per mL DSP pharmaceutical composition, such as about 70 μmol to about 120 μmol per mL) of the DSP pharmaceutical composition according to the present example in conjunction with the above Example 3. Accordingly, the pharmaceutical composition in accordance with the present disclosure indeed provides sustained release of DSP in presence of indicated lipid content to achieve balance between enhanced therapeutic efficacy and minimized side effects of a therapeutic agent, particularly to at dosing range as indicated.

What is claimed is:

1. A pharmaceutical composition for treating joint pain, the pharmaceutical composition comprising:
    (a) a lipid mixture comprising one or more phospholipids; and
    (b) an effective amount of a steroid or a pharmaceutically acceptable salt thereof;
    wherein the total amount of the one or more phospholipids is about 60 umol to about 150 umol per 1 mL of said pharmaceutical composition.

2. The pharmaceutical composition of claim 1, wherein the steroid is an intra-articular corticosteroid.

3. The pharmaceutical composition of claim 1, wherein the steroid is dexamethasone sodium phosphate, dexamethasone, betamethasone, betamethasone sodium phosphate, betamethasone acetate, betamethasone dipropioinate, betamethasone valerate, mometasone furonate, triamcinolone acetonide, triamcinolone hexacetonide, triamcinolone diacetate, methylprednisolone sodium succinate, methylprednisolone acetate, prednisolone tebutate, hydrocortisone acetate, alclometasone dipropionate, halcinonide, fluocortolone, fluocinolone acetonide or a combination thereof.

4. The pharmaceutical composition of claim 1, wherein the steroid is dexamethasone sodium phosphate.

5. The pharmaceutical composition of claim 1, wherein the lipid mixture further comprises cholesterol.

6. The pharmaceutical composition of claim 1, wherein the lipid mixture comprises dioleoylphosphatidylcholine (DOPC) and dioleoylphosphatidylglycerol (DOPG).

7. The pharmaceutical composition of claim 1, wherein the amount of the one or more phospholipids ranges from about 70 μmol to about 120 μmol per mL of the pharmaceutical composition.

8. The pharmaceutical composition of claim 1, wherein the amount of the one or more phospholipids is about 90 μmol per mL of the pharmaceutical composition.

9. The pharmaceutical composition of claim 1, wherein the total amount of the one or more phospholipids ranges from about 90 μmol to about 150 μmol per mL of the pharmaceutical composition.

10. The pharmaceutical composition of claim 1, wherein the joint pain is due to arthritis.

11. The pharmaceutical composition of claim 10, wherein the arthritis is osteoarthritis, rheumatoid arthritis, infectious arthritis, psoriatic arthritis, acute gouty arthritis, reactive arthritis, arthritis caused by Ehlers-Danlos Syndrome, haemochromatosis, hepatitis, Lyme disease, Sjogren's disease, Hashimoto's thyroiditis, celiac disease, non-celiac gluten sensitivity, inflammatory bowel disease, Henoch-Schönlein purpura, Hyperimmunoglobulinemia D with recurrent fever, sarcoidosis, Whipple's disease, TNF receptor associated periodic syndrome, Granulomatosis with polyangiitis, familial Mediterranean fever, or systemic lupus erythematosus.

12. The pharmaceutical composition of claim 4, wherein dexamethasone sodium phosphate is present in an amount ranging from about 8 mg to about 18 mg per mL of the pharmaceutical composition.

13. The pharmaceutical composition of claim 4, wherein dexamethasone sodium phosphate is present in an amount of about 12 mg per mL of the pharmaceutical composition.

* * * * *